(12) United States Patent
Bianchi et al.

(10) Patent No.: US 11,007,138 B2
(45) Date of Patent: May 18, 2021

(54) ADHESIVE POLYMER MATRIX FOR IONTOPHORESIS AND DEVICE FOR IONTOPHORESIS INCLUDING SAID MATRIX

(71) Applicant: FEELIGREEN, Grasse (FR)

(72) Inventors: Christophe Bianchi, Nice (FR); Elodie Gravelines, Juan les Pins (FR)

(73) Assignee: FEELIGREEN, Grasse (FR)

(*) Notice: Subject to any disclaimer, the term of this patent is extended or adjusted under 35 U.S.C. 154(b) by 669 days.

(21) Appl. No.: 15/560,644

(22) PCT Filed: Mar. 23, 2016

(86) PCT No.: PCT/EP2016/056336
§ 371 (c)(1),
(2) Date: Sep. 22, 2017

(87) PCT Pub. No.: WO2016/150994
PCT Pub. Date: Sep. 29, 2016

(65) Prior Publication Data
US 2018/0092834 A1      Apr. 5, 2018

(30) Foreign Application Priority Data

Mar. 24, 2015 (FR) .................................. 1552414

(51) Int. Cl.
*A61K 9/00* (2006.01)
*A61N 1/30* (2006.01)
(Continued)

(52) U.S. Cl.
CPC ............ *A61K 9/0009* (2013.01); *A61K 9/703* (2013.01); *A61K 9/7046* (2013.01);
(Continued)

(58) Field of Classification Search
CPC ................................. A61N 1/30; A61N 1/325
See application file for complete search history.

(56) References Cited

U.S. PATENT DOCUMENTS

| | | | | |
|---|---|---|---|---|
| 4,731,926 A | * | 3/1988 | Sibalis | A61N 1/044 29/877 |
| 5,147,296 A | * | 9/1992 | Theeuwes | A61N 1/0444 604/20 |

(Continued)

FOREIGN PATENT DOCUMENTS

GB           410009           5/1934

OTHER PUBLICATIONS

International Search Report for corresponding International PCT Application No. PCT/EP2016/056336, dated Jun. 9, 2016, pp. 1-9.

(Continued)

*Primary Examiner* — Jenna Zhang
(74) *Attorney, Agent, or Firm* — Pillsbury Winthrop Shaw Pittman LLP

(57) ABSTRACT

An adhesive polymer matrix for the delivery of an active principle via iontophoresis. The matrix having a first face intended to be applied onto skin and a second face intended to cooperate with electrodes. The matrix comprises electrically conductive zones and at least one electrically insulating zone, each conductive zone being insulated from another conductive zone by an insulating zone. The techniques involve the use of an electric current in order to facilitate the transdermal diffusion of active substances, and relates more particularly to an iontophoresis device.

27 Claims, 1 Drawing Sheet

(51) Int. Cl.
  *A61N 1/04* (2006.01)
  *A61K 9/70* (2006.01)
  *A61N 1/32* (2006.01)
(52) U.S. Cl.
  CPC ......... *A61N 1/0428* (2013.01); *A61N 1/0496* (2013.01); *A61N 1/30* (2013.01); *A61N 1/325* (2013.01)

(56) References Cited

U.S. PATENT DOCUMENTS

| | | | | |
|---|---|---|---|---|
| 5,162,042 | A | * | 11/1992 | Gyory ................ A61N 1/044 604/20 |
| 5,169,383 | A | | 12/1992 | Gyory et al. |
| 5,846,558 | A | * | 12/1998 | Nielsen ................ A61K 9/0009 424/448 |
| 6,119,036 | A | * | 9/2000 | Allen, Jr. ................ A61N 1/30 424/449 |
| 2003/0187339 | A1 | * | 10/2003 | Carim ................ A61N 1/30 600/372 |

OTHER PUBLICATIONS

Banerjee, et al., "Aspect of adhesives in transdermal drug delivery systems," International Journal of Adhesion & Adhesives, Dec. 31, 2013, pp. 1-15.

Perche, et al., "Accumulation and toxicity of antibody-targeted doxorubicin-loaded PEG-PE micelles in ovarian cancer cell spheroid model," Boston, MA, USA, Journal of Controlled Release, Jul. 28, 2012, pp. 1-8.

Marianecci, et al., "Anti-inflammatory activity of novel ammonium glycyrrhizinate/niosomes delivery system: Human and murine models," Rome, Italy, Journal of Controlled Release, May 18, 2012, pp. 1-9.

Alexander, et al., "Approaches for breaking the barriers of drug permeation through transdermal drug delivery," Chhattisgarh, India, Journal of Controlled Release, Jun. 14, 2012, pp. 1-15.

Ishima, et al., "Elucidation of the therapeutic enhancer mechanism of poly-S-nitrosated human serum albumin against multidrug-resistant tumor in animal models," Kumamoto University, Japan, Journal of Controlled Release, Jun. 15, 2012, pp. 1-7.

Hansen, et al., "Constrained and UV-activatable cell-penetrating peptides for intracellular delivery of liposomes," AJ Nijmegen, The Netherlands, Journal of Controlled Release, Apr. 20, 2012, pp. 1-8.

Adulnirath, et al., Cyclic RGDyk-conjugated LMWH-taurocholate derivative as a targeting angiogenesis inhibitor, Seoul, South Korea, Journal of Controlled Release, Mar. 23, 2012, pp. 1-9.

Nesseem, et al., "Development of novel transdermal self-adhesive films for tenoxicam, an anti-inflammatory drug," Egypt, Life Sciences, Aug. 13, 2010, pp. 1-9.

Deshmukh, et al., "Biodistribution and renal clearance of biocompatible lung targeted poly(ethylene glycol) (PEG) nanogel aggregates," Piscataway, NJ, Journal of Controlled Release, Aug. 4, 2012, pp. 1-9.

Kong, et al., "Magnetic targeting of nanoparticles across the intact blood-brain barrier," La Jolla, CA, Journal of Controlled Release, Jun. 4, 2012, pp. 1-9.

Nicoli, et al., "New transdermal bioadhesive film containing oxybutynin: in vitro permeation across rabbit ear skin," Parma, Italy, International Journal of Pharmaceutics 325 (2006) 2-7, Apr. 20, 2006, pp. 1-6.

Weng, et al., "Saponins modulate the intracellular trafficking of protein toxins," Berlin, Germany, Journal of Controlled Release, Aug. 28, 2012, pp. 1-13.

Padula, et al., "Single-layer transdermal film containing lidocaine: Modulation of drug release," Parma, Italy, European Journal of Pharmaceutics and Biopharmaceutics 66 (2007) 422-428, Jul. 3, 2006, pp. 1-7.

Mohammed, et al., "The Pseudomonas aeruginosa exotoxin A translocation domain facilitates the routing of CPP-protein cargos to the cytosol of eukaryotic cells," Toronto, Ontario, Canada, Journal of Controlled Release, Aug. 30, 2012, pp. 1-7.

Park, et al., "Poly-SNO-HSA: A safe and effective multifunctional antitumor agent," West Lafayette, IN, USA, Journal of Controlled Release, 2012, p. 1.

Fields et al., "Surface modified poly($\beta$ amino ester)-containing nanoparticles for plasmid DNA delivery," Yale University, USA, Journal of Controlled Release, Apr. 22, 2012, pp. 1-8.

* cited by examiner

ADHESIVE POLYMER MATRIX FOR IONTOPHORESIS AND DEVICE FOR IONTOPHORESIS INCLUDING SAID MATRIX

FIELD OF THE INVENTION

The invention relates to an adhesive polymer matrix for iontophoresis and a device for iontophoresis comprising said matrix.

The invention relates to the techniques that involve using an electric current to facilitate the transdermal diffusion of active substances, and relates more particularly to a device for iontophoresis.

PRIOR ART

Iontophoresis is a technique that can be used for cosmetic and/or medical purposes in order to introduce active substances into the dermis of the skin via a current.

Iontophoresis devices comprise tanks or patches containing the active substances to be administered. These tanks or patches are applied between the device and the skin of the user. The purpose of these devices is to carry, via the electric current, the active substances from the tank or from the patch to the dermis. The electric current must circulate between the electrodes through the dermis. However, with current devices, very little current actually circulates through the dermis. Thus, the administration of the active substance is reduced.

There is therefore a need to propose a solution that allows the delivery of the active substances to the dermis to be improved.

SUMMARY OF THE INVENTION

For this purpose, the present invention relates to an adhesive polymer matrix for iontophoresis with a first face configured to be applied onto the skin and a second opposite face configured to cooperate with electrodes. The matrix comprises electrically conductive zones and at least one electrically insulating zone, each conductive zone is electrically insulated from another conductive zone by an insulating zone.

Such a matrix ensures optimal passage of the current through the dermis. Indeed, the current circulating between two electrodes having opposite polarities can only pass through the dermis, there is no conductive passage between two conductive zones through the matrix. Thus, the matrix according to the invention allows any leakage current that negatively affects the efficiency of the iontophoresis to be eliminated. The current circulates between two conductive zones through the skin thus carrying at least one active principle to be administered.

According to another aspect, the invention relates to an iontophoresis device comprising electrodes and a source of energy, as well as a matrix as described above.

BRIEF DESCRIPTION OF THE DRAWINGS

The drawings are given as examples and are not limiting to the invention. They are schematic representations of a principle intended to facilitate the understanding of the invention and are not necessarily on the scale of the practical applications.

DETAILED DESCRIPTION OF THE INVENTION

Figure 1:
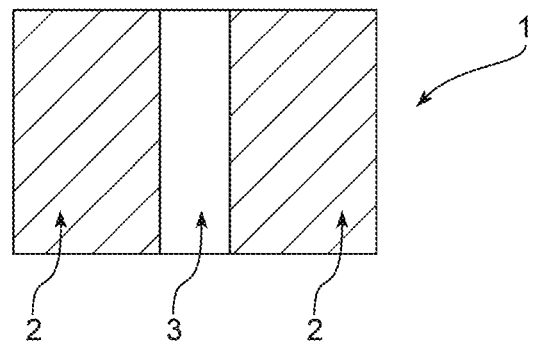
FIG. 1 shows an overhead view of an example of the arrangement of the conductive and insulating zones of a matrix according to the invention.
Figure 2:
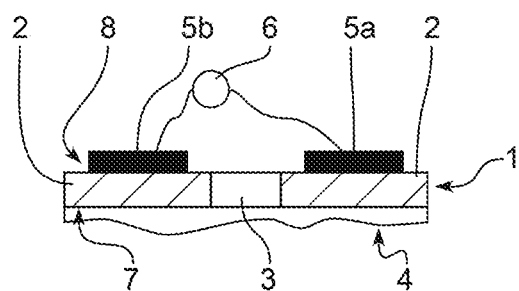
FIG. 2 shows a cross-sectional view of the device according to the invention applied onto the skin.
Figure 3:
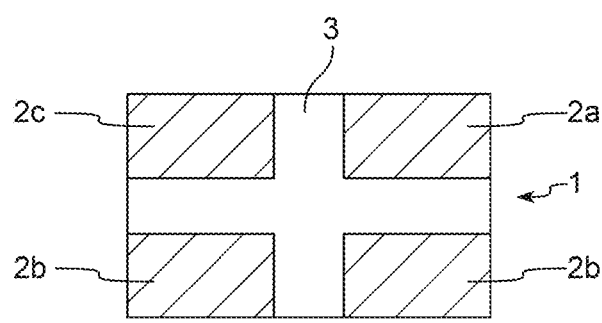
FIG. 3 shows an overhead view of another example of the arrangement of the conductive and insulating zones of a matrix according to the invention.

Before beginning a detailed review of embodiments of the invention, optional features that can optionally be used together or alternatively are listed below.

First of all, it is recalled that the invention relates to an adhesive polymer matrix via the delivery of an active principle for iontophoresis, having a first face intended to be applied onto the skin and a second face intended to cooperate with electrodes, characterised in that it comprises electrically conductive zones and at least one electrically insulating zone, each conductive zone being insulated from another conductive zone by an insulating zone.

Advantageously, the matrix according to the invention is such that the conductive zones comprise at least one active principle to be delivered.

Advantageously, the conductive zones are configured to cooperate with electrodes providing an electric current, the at least one active principle of each conductive zone being chosen according to the polarisation of the electrode cooperating with said zone.

Advantageously, the conductive zones comprise different active principles.

Advantageously, the at least one insulating zone has a minimum width of 1 mm separating two conductive zones.

Advantageously, the zones extend over the entire thickness of the matrix.

Advantageously, the matrix comprises at least one polymer, at least one adhesive and at least one plasticizer.

Advantageously, the matrix comprises an absorption promoter.

The invention also relates to a device for iontophoresis, comprising at least two electrodes and a source of energy electrically connected to the electrodes, characterised in that it comprises an adhesive polymer matrix. Advantageously, the conductive zones of the adhesive polymer matrix are connected to the electrodes.

The invention relates to an adhesive polymer matrix for iontophoresis. The matrix 1 comprises a first face 7 and a second opposite face 8. The first face 7 is intended to be applied onto the skin of the user, advantageously at the area to be treated. The second face 8 is configured to cooperate with an iontophoresis device and more particularly with electrodes 5a, 5b.

The iontophoresis device comprises electrodes 5a, 5b and a source of energy 6. The device can be in various form, whether only electrodes electrically connected to a remote source of energy or in the form of a case or a patch such as those described in previous patent applications of the applicant. Advantageously, the device comprises an electronic module, advantageously activation means such as, for example, a control button. The electronic module advantageously comprises control means and means of measurements of physiological parameters for example for measurement of the temperature, the pH, the pressure, the relative humidity, the resistivity.

The electronic module is advantageously intended to control the current provided to the electrodes 5a, 5b. The electronic module advantageously allows the intensity, the voltage and/or the administration time to be controlled. According to one possibility, the electronic module comprises a microprocessor.

According to one possibility, the source of energy 6 is a source of electric energy such as a rechargeable accumulator or a battery allowing a voltage to be applied to the electrodes 5a, 5b for example via a voltage generator. The source of energy 6 can be varied. Advantageously, the source of energy 6 is independent, for example an independent generator of energy via energy recovery or batteries can be used.

According to an advantageous embodiment, the electronic module comprises the source of energy, preferably a source of current advantageously independent. This arrangement is particularly advantageous for allowing ambulatory use of the device according to the invention.

The device is advantageously configured to deliver a current having a controlled intensity. Preferably, the intensity I is less than or equal to 1 mA.

The electrodes 5a, 5b allow an electric current to be transmitted to the skin 4 by passing through the matrix 1 advantageously along its thickness and more particularly of the conductive zones 2 described below.

The device of the invention advantageously comprises a step-up transformer. The step-up transformer is advantageously present in the electronic module. The step-up transformer allows the voltage provided to the electrodes to be stepped up from the voltage delivered by the source of energy.

According to a preferred embodiment, the matrix 1 can be separated from the device, that is to say, is removable. Preferably, the device is reusable. The matrix 1 is advantageously a consumable that is used a single time or several times, but fewer times than the device. The matrix is disposable. This is of particular interest from an ecological and economic point of view since the device comprises the electrodes 5a, 5b.

The device according to the invention provides a device that can both be a single-use device or at least be used for a single patient while reusing the costly electronic elements.

According to the invention, the matrix 1 is a flexible cloth. The flexibility is such that two opposite points of the contour can be joined together without damaging the matrix 1. This flexibility is advantageously maintained when the device is connected to and fastened onto the matrix 1.

Preferably, the matrix 1 has a thickness from 25 to 60 μm. The flexibility of the matrix allows the matrix to conform to the zone of application of the body onto which it is intended to be applied.

The device and the matrix 1 according to the invention are usable on all the areas of the human body easily and without difficulty or discomfort for the user.

The matrix 1 comprises at least active principle intended to be administered to the skin 4 of the user. Active principle means a substance having a therapeutic or cosmetic effect on the user.

The matrix 1 according to the invention comprises electrically conductive zones 2 and at least one electrically insulating zone. Thus, the conductive zones 2 are insulated from each other by at least one insulating zone 3. Advantageously, the conductive zones 2 cooperate with electrodes 5a, 5b of an iontophoresis device.

The conductive zones 2 are configured to allow electrical conduction between the electrodes 5a 5b of the device and the skin onto which the matrix 1 is applied. The electric current passes through the matrix 1 from the second face 8 to the first face 7 that is to say along the thickness of the matrix 1.

The insulating zones 3 are configured to allow insulation from electrical conduction, in particular between the conductive zones 2.

For example, the presence of ionised active principle in a conductive zone 2 of the matrix 1 is sufficient to confer the property of electrical conduction onto said zone. On the contrary, the absence of an ionised active principle and preferably of any other ionised element in the insulating zone 3 is sufficient to confer a property of resistance to electrical conduction onto said zone.

According to the method for manufacturing the matrix 1 described below, the matrix 1 comprises a film, for example of silicone, forming the base of the matrix 1. This film is embedded in the polymer of the polymer matrix.

The conductive zones 2 and insulating zone 3 are formed over the entire thickness of the matrix 1.

Preferably, the conductive zones 2 contain at least one active principle.

Preferably, the insulating zones 3 does not comprise any active principle.

According to a preferred possibility, the active principles of each conductive zone 2 are chosen according to the polarisation of the electrode 5a, 5b cooperating with said zone.

Advantageously, the electrodes are chosen in order to have at least one electrode having a polarity opposite to at least one other, preferably having an opposite polarity two by two, in such a way as to allow circulation of the electric current from a conductive zone 2 to another conductive zone 2 through the skin.

An insulating zone 3 separating at least two conductive zones 2 has a minimum width of 1 mm in order to provide satisfactory insulation 25.

According to one embodiment, the matrix 1 comprises a plurality of conductive zones 2a, 2b, 2c, 2d . . . separated by at least one insulating zone 3. Each conductive zone comprises a different active principle chosen according to the polarisation of the cooperating electrode 5. According to one possibility, the matrix 1 is configured to allow sequential iontophoresis. This means that the active principles of each conductive zone 2 are administered sequentially. The device is configured to provide current to the conductive zones 2 via the electrodes 5, sequentially which allows active principles to be administered one after the other in such a way as to improve the treatments.

Each conductive zone 2a, 2b, 2c and 2d is connected to at least one electrode 5a, 5b, respectively.

For example, in a conductive zone 2 configured to cooperate with a cathode electrode 5a, the active principles are chosen from the following list opposite which are indicated examples of diseases, symptoms or indications for which these active principles could be used:
  penicillin,
  sulphonamides 10%: furuncles,
  nicotinic acid,
  potassium iodide 1 to 3%: anti-sclerotic, vascular tonic, anti-arthrosis, nerve tonic, fibrolytic, tonic of the sympathetic nervous system, vascular tonic, hypertrophic scar, arterial sclerosis, arthrosis, arthritis, sequelae from hemiplegia without contracture, peripheral nervous lesion,
  sodium iodide 1 to 3%: anti-sclerolytic, adherent scars, cheloids, joint stiffness, Dupuytren's contracture, sodium salicylate 1 to 3%: anti-rheumatic, antalgic, anti-oedematous, joint arthrosis, PSH, neuralgia, periphlebitis,
sublimed sulphur,
hyaluranidase 150u 1 vial: diffusing agent, anti-oedematous, local oedemas, effusions, lymphangitis,
hydrocortisone 1%: steroidal anti-inflammatory, rheumatic inflammations without signs of osteoporosis,
prednisolone succinate 1%: steroidal anti-inflammatory, rheumatic inflammations without signs of osteoporosis, steroidal anti-inflammatory,
celestene: steroidal anti-inflammatory, rheumatic inflammations without signs of osteoporosis,
Betamethasone: steroidal anti-inflammatory+mucopolysaccharidase, arthrosis, chronic joint diseases, tendinitis, para-articular diseases, Dupuytren's contracture and Peyronie's disease, cheloids, tendinitis,
percutalgine: steroidal anti-inflammatory, rheumatic inflammations without signs of osteoporosis, arthritis, joint disease,
ketoprofen: non-steroidal anti-inflammatory drug,
profenid 50 to be associated with a mucopolysaccharidase: arthrosis, para-articular disease,
dicloflenac 7: non-steroidal anti-inflammatory drug,
voltaren—to be associated with a mucopolysaccharidase: abarticular diseases,
phenylbutazone: non-steroidal anti-inflammatory drug,
butazolidine: rheumatic inflammations, post-traumatic inflammations,
salicylate of lithia 1%: anti-uricemic, gouty and para-gouty diseases,
mucopolysaccharidase: diffusing agent, cellulite, oedema, hematoma, base for penetration of anti-inflammatory products,
idrocilamide: muscle relaxant,
srilane: anti-inflammatory,
brolitene: muscle contractures, pain, tendinitis,
thiomucase: anti-oedematous, resolvent, lymphoedema, cellulite,
euclidan: anti-inflammatory, vasodilator, algoneurodystrophy, peripheral circulation,
nicometat 2 amp: anti-inflammatory, algoneurodystrophy,
alphamucase: anti-oedematous, algoneurodystrophy,
calcium chloride: fibrolytic, scars,
sodium chloride: fibrolytic, scars,
thriodothryacetique acid: lipolytic, cellulite, For example, in a conductive zone 2 configured to cooperate with an anode electrode 5b, the active principles are chosen from the following list opposite which are indicated examples of diseases, symptoms or indications for which these active principles could be used:
carbaïne 5%: local anaesthesia, hyperalgesia,
chlorproethazine: muscle relaxant,
neuriplege: contractures, spasmophilia, myalgia,
tetanil: muscle relaxant, spasmophilia,
alphachymotrypsine: diffusing agent, anti-oedematous, contusions, sprains, oedemas,
alphacutanee: diffusing agent, anti-oedematous, contusions, oedemas,
freeze-dried thyroid: lypolitic, lipid cataboliser, obesity,
triodothryoacetique acid: lypolitic, obesity,
lnflanil: anti-rheumatic, arthritis, tendinitis, articular disease,
organic silica: regenerator of connective tissue, stretch marks, localized cellulite,
salicylate of lithia: anti-rheumatic, arthrosis of the small joints,
adrenaline: vasoconstrictor, peripheral circulation,
aconitine nitrate: anti-neuralgic, antalgic, neuralgia of the trigeminal nerve, postherpetic neuralgia,
percutalgine: antalgic, back pain, ligament pain, tendon pain,
apisin, apicure (bee venom): intercostal neuralgia,
silver nitrate: articular anti-rheumatic,
acetylcholine 0.5%,
vitamin B,
calcium chloride: sedative, recalcifying, algesia, spastic hemiplegia, osteoporosis, spasmophilia, algoneurodystrophy, joint stiffness,
zinc chloride: antiseptic, chronic conjunctivitis, gynaecology, ENT,
zinc sulphate: gynaecology, ENT,
magnesium chloride: sedative, spasmolytic, spasmophilia, plane warts,
magnesium sulphate: spasmophilia, plane warts,
ammonium chloride: fibrolytic, joint stiffness,
flaxedyl: synthetic curare-like agent, muscle relaxant, contractures, torticollis, dorsalgia, lombalgia, rheumatic muscle contractures, spasmophilia,
doryl 0.1%,
histamine chlorydrate: revulsive, hyperalgesia, sciatica,
histamine bichlorydrate: revulsive, vasodilator, joint disease,
epinephrine phosphate: vasoconstrictor, asthma, peripheral circulation,
copper sulphate: antiseptic, fungicidal, mycoses,
cocaine,
procaine,
novocaine: local anaesthesia, antalgic, neuralgia of the trigeminal nerve, shingles,
potassium citrate: spasmophilia, plane warts,
percaine 2 to 5%,
priscol 5 to 10%,
radon 1 00000 EM,
corticosteroids 1%: joint rheumatism, (celestene, betnesol), gout,
hydrocortisone 1%: joint rheumatism, gout,
histacone,
penicillin,
bromine,
biomycine,
butazoline,
streptomyline, The matrix 1 advantageously comprises at least one polymer chosen from polyurethane, for its elasticity, polysiloxane for its insulating ability, Poly(methyl methacrylate) for its physical strength and transparency, Poly(vinyl alcohol) for its hydrophilic properties and its strength, Polyethylene for its hardness, its robustness and its swelling, Polyvinylpyrrolidone for its suspension abilities.

Preferably, the matrix 1 is adhesive that is to say that it is configured to be glued onto or to adhere, temporarily, to the skin onto which is it applied. For this purpose, the matrix 1 comprises at least one adhesive chosen from acrylic acid, the polyacrylates, polyisobutylene, polyvinylpyrrolidone, the silicones.

According to one embodiment, the matrix 1 comprises at least one plasticiser chosen from sorbitol, glycerol, propylene glycol.

According to one possibility, the matrix 1 comprises a solvent.

According to one embodiment, the matrix 1 comprises an absorption promoter chosen from water, alcohols, fatty alcohols such as propylene glycol, amino acids, amides, esters, ethers such as PEG, terpenes, terpenoids and essential oils, sulphoxides, lipids.

According to a preferred embodiment, the matrix 1 is prepared using the following method. A solution of adhesive is mixed with a solution of polymer in order to form a mixture A. Then, a solution comprising a plasticiser and at least one active principle is added to the mixture A in order to form the mixture B. The mixture B is stirred slowly, at a speed advantageously lower than 200 rpm, for a time equivalent to one night. The mixture is then poured onto at least a portion of a film for example of silicone.

The manufacturing is carried out via screen printing. These steps are repeated in order to form another conductive zone 2 and the insulating zone 3, respectively, on portions of the same film for example of silicone. The assembly is dried in a drying oven for example for 30 minutes at 80° C. The matrix 1 obtained should be preserved in a desiccator.

According to the embodiment in which the matrix 1 comprises a plurality of conductive zones 2a, 2b, 2c, 2d comprising various active principles, respectively. The steps described above are carried out for each of the conductive zones.

The device according to the invention can be used in cosmetic or therapeutic uses. If the device is used for iontophoresis, it intended to make active substances penetrate into the dermis, for example such as vitamin A or retinol having a depigmenting effect, lidocaine having a local anaesthetic effect, hyaluronic acid having regenerative and scarring property, retinoic acid for the treatment of acne, vitamin C having an antioxidant effect, a chelating agent for ions such as β-alanine diacetic acid for the treatment of erythemas, glycolic acid improving the texture of the skin, dexamethasone sodium phosphate having an anti-inflammatory effect or any other type of active ingredient that is ionised or in the form of anionic or cationic emulsions in order to be able to be carried by the current.

According to an advantageous possibility, the device comprises a plurality of anodes and a plurality of cathodes alternating with the anodes. In this configuration, the total current is divided into a plurality of anode-cathode circuits in such a way that the density of the current circulating from an anode to a cathode is preferably less than 1 mA/cm2. Moreover, in order to prevent the formation of external field lines, that is to say, outside of the device, the two electrodes at the two ends have the same polarity, that is to say, these are two anodes or two cathodes.

REFERENCES

1 Matrix
2 Conductive zone
3 Insulating zone
4 Skin
5a. 5b. Electrodes
6 Source of energy
7 First face
8 Second face

The invention claimed is:

1. An adhesive polymer matrix for the delivery of an active principle via iontophoresis, the matrix having a first face configured to be applied onto skin and a second face configured to cooperate with electrodes, the matrix comprising electrically conductive zones and at least one electrically insulating zone, each conductive zone of the electrically conductive zones being insulated from another conductive zone by one of the at least one insulating zone and wherein the at least one insulating zone comprises a mixture of materials including at least one polymer and at least one adhesive.

2. The matrix according to claim 1, wherein the electrically conductive zones each comprise at least one active principle to be delivered.

3. The matrix according to claim 2, wherein the electrically conductive zones comprise different active principles.

4. The matrix according to claim 2, wherein the electrically conductive zones are configured to cooperate with said electrodes providing an electric current, the at least one active principle of each electrically conductive zone of the electrically conductive zones being chosen according to the polarisation of the electrode cooperating with said respective electrically conductive zone.

5. The matrix according to claim 2, wherein the at least one insulating zone has a minimum width of 1 mm separating two electrically conductive zones.

6. The matrix according to claim 2, wherein the electrically conductive zones and the at least one electrically insulating zone extend over the entire thickness of the matrix.

7. The matrix according to claim 1, wherein the electrically conductive zones are configured to cooperate with said electrodes providing an electric current, the at least one active principle of each electrically conductive zone of the electrically conductive zones being chosen according to the polarisation of the electrode cooperating with said respective electrically conductive zone.

8. The matrix according to claim 7, wherein the electrically conductive zones comprise different active principles.

9. The matrix according to claim 1, wherein the at least one insulating zone has a minimum width of 1 mm separating two electrically conductive zones.

10. The matrix according to claim 1, wherein the electrically conductive zones and the at least one electrically insulating zone extend over the entire thickness of the matrix.

11. The matrix according to claim 1, comprising at least one plasticiser.

12. The matrix according to claim 11, further comprising an absorption promoter.

13. The matrix according to claim 11, wherein the at least one plasticiser comprises sorbitol or glycerol.

14. The matrix according to claim 1, wherein the at least one polymer is polyurethane, polysiloxane, poly(methylmethacrylate), poly(vinyl alcohol), polyethylene or polyvinylpyrrolidone.

15. The matrix according to claim 1, wherein the at least one adhesive is acrylic acid, a polyacrylate, polyisobutylene, polyvinylpyrrolidone or a silicone.

16. The matrix according to claim 15, wherein the at least one adhesive is a polyacrylate.

17. The matrix according to claim 1, wherein at least one of the electrically conductive zones and the at least one insulating zone are formed using a same base solution that includes the at least one adhesive and the at least one polymer.

18. A device for iontophoresis, comprising at least two electrodes and a source of energy electrically connected to the at least two electrodes, comprising an adhesive polymer matrix according to claim 1.

19. The device according to claim 18, wherein the electrically conductive zones of the adhesive polymer matrix are connected to the at least two electrodes.

20. An adhesive polymer matrix for the delivery of an active principle via iontophoresis, the matrix having a first face configured to be applied onto skin and a second face configured to electrically connect with electrodes, the matrix comprising:
- more than one electrically conductive zones; and
- at least one electrically insulating zone adjacent two electrically conductive zones of the more than one electrically conductive zones,
- wherein the at least one electrically insulating zone comprises a mixture of materials including at least one polymer and at least one adhesive.

21. The matrix according to claim 20, wherein the at least one electrically insulating zone is between two electrically conductive zones of the more than one electrically conductive zones.

22. The matrix according to claim 20, wherein each electrically conductive zone of the more than one electrically conductive zones comprises at least one active principle for delivery to the skin.

23. The matrix according to claim 20, wherein the at least one electrically insulating zone has a width of 1 mm.

24. The matrix according to claim 20, wherein the matrix has a thickness ranging from 25 µm to 60 µm.

25. The matrix according to claim 20, further comprising:
- at least one active principle applied to at least one electrically conductive zone of the more than one electrically conductive zones.

26. The matrix according to claim 20, wherein the at least one polymer is polyurethane, polysiloxane, poly(methylmethacrylate), poly(vinyl alcohol), polyethylene or polyvinylpyrrolidone.

27. The matrix according to claim 20, wherein the at least one adhesive is acrylic acid, a polyacrylate, polyisobutylene, polyvinylpyrrolidone or a silicone.

* * * * *